United States Patent [19]

Kiessling

[11] Patent Number: 5,618,664
[45] Date of Patent: Apr. 8, 1997

[54] PROCESS FOR SIMULTANEOUSLY DISINFECTING AND FIXING BIOLOGICAL FLUIDS

[76] Inventor: Ann A. Kiessling, 53 Concord Rd., Bedford, Mass. 01730

[21] Appl. No.: 408,137

[22] Filed: Mar. 21, 1995

Related U.S. Application Data

[63] Continuation of Ser. No. 147,022, Nov. 2, 1993, abandoned.

[30] Foreign Application Priority Data

Nov. 3, 1992 [GB] United Kingdom ............... 9223035

[51] Int. Cl.$^6$ ............... A01N 1/02; A01N 35/00; A61L 2/00; C12Q 1/22
[52] U.S. Cl. .................. 435/2; 435/6; 435/31; 435/32; 435/91; 435/810; 422/28; 422/29; 422/36; 514/693; 514/694
[58] Field of Search ............... 435/2, 6, 31, 32, 435/91, 810; 422/28, 29, 36; 514/693, 694

[56] References Cited

U.S. PATENT DOCUMENTS

| | | | |
|---|---|---|---|
| 4,675,159 | 6/1987 | Al-Sioufi | 422/36 |
| 4,683,202 | 7/1987 | Mullis | 435/91 |
| 4,880,602 | 11/1989 | Al-Sioufi | 422/36 |
| 5,422,277 | 6/1995 | Connelly et al. | 436/10 |

OTHER PUBLICATIONS

Aloisio et al, *J. Immunol. Methods*, vol. 128, pp. 281–285, 1990.
Lifson et al, *J. Immunol. Methods*, vol. 86, pp. 143–149, 1986.
Li et al, *Proc. Natl. Acad. Sci. USA*, vol. 87, pp. 4580–4584, Jun. 1990.
Nicholson et al, *J. Immunol. Methods*, vol. 160, pp. 215–218, 1993.
M. Borzy et al., Detection of Human Immunodeficiency Virus in Cell-Free Seminal Fluid, J. of Acquired Immune Deficiency Syndromes, vol. 1, 1988, 419–424.
A. Kiessling et al., Human Immunodeficiency Virus Detection and Differential Leukocyte Counts are Accurate and Safer with Formaldehyde-Fixed Blood, Blood, vol. 81, 1993, 864–865.
L. Fitzgerald et al., PCR Amplification of HIV and Cellular DNA Sequences in Formaldehyde-Fixed, Immunoreactive White Blood Cells, BioTechniques, vol. 15, No. 1, 1993, 128–133.
A. Kiessling et al., Formaldehyde-fixed semen is suitable and safer for leukocyte detection and DNA amplification, Fertility and Serility, vol. 60, No. 3, Sep. 1993, 576–581.
J. Lifson et al., Utility of formaldehyde fixation for flow cytometry and inactivation of the AIDS associated retrovirus, J. of Immunological Methods, vol. 86, 1986, 143–149.
L. Martin et al., Disinfection and Inactivation of the Human T Lymphotropic Virus Type III/Lymphadenopathy–Associated Virus, J. of Infectious Diseases, vol. 152, No. 2, 1985, 400–403.
B. Spire et al., Inactivation of Lymphadenopathy Associated Virus by Chemical Disinfectants, The Lancet, Oct. 20, 1984, 899–901.
C. Aloisio et al., Recovery of infectious human immunodeficiency virus from cells treated with 1% paraformaldehyde, J. of Immunological Methods, vol. 128, 1990, 281–285.
J. Cory et al., Detection of human immunodeficiency virus–infected lymphoid cells at low frequency by flow cytometry, J. of Immunological Methods, vol. 105, 1987, 71–78.
L. Lanier et al., Paraformaldehyde Fixation of Hematopoietic Cells for Quantitative Flow Cytometry (FACS) Analysis, J. of Immunological Methods, vol. 47, 1981, 25–30.
M. Lai–Goldman et al., Detection of human immunodeficiency virus (HIV) infection in formalin–fixed, paraffin–embedded tissues by DNA amplification, Nucleic Acids Research, vol. 16, No. 16, 1988, 8191.
D. Shibata et al., Analysis of Human Immunodeficiency Virus and Cytomegalovirus Infection by Polymerase Chain Reaction in the Acquired Immunodeficiency Syndrome, Arch Pathol Lab Med, vol. 113, Nov. 1989, 1239–1244.
M. Holodniy et al., Detection and Quantification of Human Immunodeficiency Virus RNA in Patient Serum by Use of the Polymerase Chain Reaction, J. of Infectious Diseases, vol. 163, 1991, 862–865.
C. Lynch et al., Detection of HIV–1 DNA by PCR: Evaluation of Primer Pair Concordance and Sensitivity of a Single Primer Pair, J. of Acquired Immune Deficiency Syndromes, vol. 5, 1992, 433–440.
M. Poznansky et al., A Rapid Method for Quantitating the Frequency of Peripheral Blood Cells Containing HIV–1 DNA, J. of Acquired Immune Deficiency Syndromes, vol. 4, 1991, 368–373.
K. Young et al., Detection of HIV DNA in peripheral blood by the polymerase chain reaction: a study of clinical applicability and performance, AIDS, vol. 4, No. 5, 1990, 389–391.
B. Conway et al., Detection of HIV–1 DNA in Crude Cell Lysates of Peripheral Blood Mononuclear Cells by the Polymerase Chain Reaction and Nonradioactive Oligonucleotide Probes, J. of Acquired Immune Deficiency Syndromes, vol. 3, 1990, 1059–1064.
J.P. Clewley, The polymerase chain reaction, a review of the practical limitations for human immunodeficiency virus diagnosis J. of Virological Methods, vol. 25, 1989, 179–186.
C. Ou et al., DNA Amplification of Direct Detection of HIV–1 in DNA of Peripheral Blood Mononuclear Cells, Science, vol. 239, Jan. 15, 1988, 295–297.

(List continued on next page.)

*Primary Examiner*—Elizabeth C. Weimar
*Assistant Examiner*—Abdel A. Mohamed
*Attorney, Agent, or Firm*—Wolf, Greenfield & Sacks, P.C.

[57] ABSTRACT

Methods and kits for reducing the transmission of infectious agents contained in biological fluid samples are provided. The methods include contacting the biological sample with a fixative solution containing a fixative present at a concentration sufficient to simultaneously disinfect the sample and fix analytes contained therein.

26 Claims, 3 Drawing Sheets

OTHER PUBLICATIONS

S. Kwok et al., Identification of Human Immunodeficiency Virus Sequences by Using In Vitro Enzymatic Amplification and Oligomer Cleavage Detection, J. of Virology, May 1987, 1690–1694.

M. DaSilva et al., Detection of HIV–Related Protein in Testes and Prostates of Patients with AIDS, A.J.C.P., vol. 93, No. 2, Feb. 1989, 196–201.

M. El–Demiry et al., Identifying Leucocytes and Leucocyte Subpopulations in Semen Using Monoclonal Antibody Probes, Urology, vol. 28, No. 6, Dec. 1986, 492–496.

R. Warnke et al., Diagnosis of Human Lymphoma with Monoclonal Antileukocyte Antibodies, New England J. of Medicine, vol. 309, No. 21, Nov. 24, 1983, 1275–1281.

Lifson, J.D. et al., Variables Affecting T–Lymphocyte Subsets in a Volunteer Blood Donor Population, Clin. Clin. Immunol and Immunopathol. 36:151–156 (1985).

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: primer for amplifying a conserved region of HIV I (Genbank Accession No. K02007).

( i i i ) HYPOTHETICAL: NO ( i v ) ANTI-SENSE: NO ( x i ) SEQUENCE DESCRIPTION: SEQ ID NO:1:

TTATCAGAAG GAGCCACCCC     20

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: primer for amplifying a conserved region of HIV I (Genbank Accession No. K02007).

( i i i ) HYPOTHETICAL: NO ( i v ) ANTI-SENSE: NO ( x i ) SEQUENCE DESCRIPTION: SEQ ID NO:2:

CCTTGTCTTA TGTCCAGAAT GC     22

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: primer for amplifying a conserved region of HIV I (Genbank Accession No. K02007).

( i i i ) HYPOTHETICAL: NO ( i v ) ANTI-SENSE: NO ( x i ) SEQUENCE DESCRIPTION: SEQ ID NO:3:

AGTGGGGGGA CATCAAGCAG CCATGCAAAT     30

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: primer for amplifying a conserved region of HIV I (Genbank Accession No. K02007).

( i i i ) HYPOTHETICAL: NO ( i v ) ANTI-SENSE: NO ( x i ) SEQUENCE DESCRIPTION: SEQ ID NO:4:

CCTGCTATGT CACTTCCCCT            20

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: primer for amplifying a conserved region of HIV I (Genbank Accession No. K02007).

( i i i ) HYPOTHETICAL: NO ( i v ) ANTI-SENSE: NO ( x i ) SEQUENCE DESCRIPTION: SEQ ID NO:5:

GAGACTATCA ATGAGGAAGC            20

( 2 ) INFORMATION FOR SEQ ID NO:6:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: primer for amplifying a conserved region of HIV I (Genbank Accession No. K02007).

( i i i ) HYPOTHETICAL: NO ( i v ) ANTI-SENSE: NO ( x i ) SEQUENCE DESCRIPTION: SEQ ID NO:6:

TGCTATGTCA GTTCCCCTTG GTTCTCT            27

( 2 ) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Other nucleic acid
    ( A ) DESCRIPTION: LDL receptor specific primer derived from Genbank Accession No. L00347K02573.

( i i i ) HYPOTHETICAL: NO ( i v ) ANTI-SENSE: NO ( x i ) SEQUENCE DESCRIPTION: SEQ ID NO:7:

AGTGCCAACC GCCTCACAG            19

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid
      ( A ) DESCRIPTION: LDL receptor specific primer
         derived from Genbank Accession No. L00348K02573.

( i i i ) HYPOTHETICAL: NO ( i v ) ANTI-SENSE: NO ( x i ) SEQUENCE DESCRIPTION: SEQ ID NO:8:

CCTCTCACAC CAGTTCACTC                            2 0

( 2 ) INFORMATION FOR SEQ ID NO:9:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid
      ( A ) DESCRIPTION: LDL receptor specific primer
         derived from Genbank Accession No. L00348K02573.

( i i i ) HYPOTHETICAL: NO ( i v ) ANTI-SENSE: NO ( x i ) SEQUENCE DESCRIPTION: SEQ ID NO:9:

TGGCTGGGTG AGGTTGTGGA                            2 0

PROCESS FOR SIMULTANEOUSLY DISINFECTING AND FIXING BIOLOGICAL FLUIDS

GOVERNMENT SUPPORT

This work was funded by a grant from the U.S. Public Health Service National Institute of Health, grant number CA 53899.

This application is a continuation of Ser. No. 08/147,022, filed Nov. 2, 1993, now abandoned.

FIELD OF THE INVENTION

This invention relates to processes and kits for handling biological fluid samples to reduce the transmission of infectious agents contained therein. More particularly, the invention relates to the use of a fixative at a disinfecting concentration to simultaneously disinfect the sample and to fix clinically-relevant analytes contained in the sample.

BACKGROUND OF THE INVENTION

Peripheral blood and semen are principle sources of transmission of many human pathogens, including Human Immunodeficiency Virus (HIV), Human T Cell Leukemia Viruses (HTLVs), hepatitis B and hepatitis C in addition to the more widely recognized sexually transmitted diseases such as gonorrhea, syphilis and chlamydiasis. Blood samples are frequently used to diagnose these diseases, principally by an automated laboratory test which identifies pathogen-specific proteins or antibodies contained in serum samples. Semen is rarely used as a diagnostic fluid unless the individual is being evaluated for fertility because of the relative logistical ease of obtaining blood samples and the large reference base for normal blood values, in contrast to the relative difficulty in obtaining and evaluating semen samples and the lack of a reference base for semen pathogens. Thus, even diseases of male reproductive tract organs directly involved with semen production (e.g. carcinoma of the prostate) are rarely, if at all, diagnosed or evaluated by analyzing semen samples.

Current laboratory safety practices (termed Universal Precautions) include wearing gloves, masks, goggles and laboratory coats when opening or handling blood tubes, but no general scheme for pathogen inactivation prior to blood handling at a testing facility is currently available. Universal Precautions are the only andrology laboratory safety practices currently available for the safe handling of semen samples.

in general, two types of blood samples are routinely obtained by venipuncture in clinical blood drawing stations: (1) samples intended to yield cell-free serum or plasma for antigen or antibody measurements and (2) samples in which coagulation is blocked by anticoagulants such as heparin or chelating agents (salts of citric acid or ethylenediaminetetraacetic acid, EDTA) for evaluation of peripheral blood cells. Anticoagulated blood samples are used for evaluation of cellular blood components such as platelets, red blood cells and the various classes of leukocytes. Leukocytes are differentiated by morphology (either by automated instrument or by a technician looking at a smear in a microscope), by specific surface antigens (such as the CD4 or CD8 receptors on some lymphocyte subtypes) or by nuclear DNA content (as assessed, for example, by flow cytometry).

Semen generally is collected by spontaneous ejaculation into a condom during intercourse or into a sterile laboratory container following masturbation. To discover possible causes of infertility or to verify vasectomy or vasectomy reversal, ejaculated semen is evaluated in andrology laboratories for cell type and concentration and for seminal fluid composition with respect to typical semen components (e.g., zinc, fructose) and the possible presence of anti-sperm antibodies and pathogens. Seminal fluid also contains leukocytes and other cells such as prostate and seminal vesicle cells in addition to mature and immature germ cells. Automated sample analysis is not currently available for semen samples. Accordingly, semen analysis is labor intensive, requiring substantial sample handling and processing by laboratory personnel.

In summary, all aspects of handling blood and semen samples expose health care personnel to potentially infectious pathogens. In addition to the potential for infection, blood and serum samples pose unique problems for the accurate and sensitive analysis of clinically-relevant analytes. For example, although amplification of selected DNA sequences by polymerase chain reaction (PCR) is a powerful diagnostic tool for the identification of genetic mutations, wide clinical application of the technique to the analysis of biological fluids for detection of infectious agents has been delayed due to a number of factors, including problems inherent in collecting and transporting infectious samples and the complexity and expense of the amplification technique. Thus, although a number of publications have reported using the polymerase chain reaction to detect single copies of human immunodeficiency virus (HIV) genes in isolated DNA, PCR amplification of DNA in HIV-infected peripheral blood samples requires leukocyte isolation (e.g., by centrifugation techniques, such as Ficoll gradients) and/ or cellular DNA purification (e.g., using reagents such as guanidium isothiocyanate) prior to amplification and detection of HIV-specific DNA sequences. Such extensive sample preparation reportedly is necessitated by the inhibitory effect of blood components (e.g., hemoglobin) on the amplification reaction. As a result, application of the PCR method to the analysis of biological fluid samples increases the risk of transmission of infectious agents to laboratory personnel.

The wide spread application of PCR for analyzing biological fluid samples additionally has been delayed because of the capital expense associated with creating and maintaining an adequately-equipped laboratory for practising amplification on a biological fluid sample, i.e., the laboratory must be equipped for pathogen containment, DNA purification and radiolabeled oligonucleotide probes in order to achieve the sensitivity necessary to detect single copies of provirus in a background of large copy numbers of cellular DNA.

In view of the foregoing, there is still a need for methods for safely handling, transporting and analyzing potentially infectious biological fluid samples. Such methods would permit the disinfection of infectious agents contained in the biological fluid sample at the time of sample collection, thereby minimizing the risk of transmission to laboratory personnel.

SUMMARY OF THE INVENTION

The present invention overcomes the problems inherent in the prior art by providing methods for handling biological fluid samples to reduce the exposure of health care personnel to infectious agents, while preserving the analytes contained therein for analysis. The methods involve contacting the sample with a fixation solution containing a fixative that is present at a disinfecting concentration. Also provided are kits for collecting and disinfecting the biological fluid sample at the collection site. The instant invention was initially disclosed in Great Britain Patent Application No. GB 9223035.8, filed Nov. 3, 1992, the entire contents of which are incorporated herein by reference.

According to one aspect of the invention, a method for handling a biological fluid sample is provided. The method includes collecting the sample from a donor at a first location, contacting the sample at the first location with a fixation solution containing a fixative to form a fixed specimen, and packaging the fixed specimen for transport to a second location for analysis. The fixation solution contains a disinfecting concentration of fixative. Contacting the fixation solution with the sample simultaneously disinfects the sample and preserves analytes contained therein for analysis. Typically, the biological fluid sample is a blood or semen sample collected from a human donor and the fixative is one of several fixatives commonly used by pathologists for preserving tissue samples. Exemplary fixatives include formaldehyde, paraformaldehyde and glutaraldehyde. In a preferred embodiment, the fixative is paraformaldehyde, with the disinfecting concentration of paraformaldehyde being between about two and about four percent.

According to another aspect of the invention, a method for simultaneously disinfecting a biological sample including red blood cells and leukocytes, lysing the red blood cells and fixing the leukocytes is provided. The method includes contacting the biological sample with a fixation solution containing a fixative to form a fixed specimen. The fixation solution has an osmolarity that is sufficient to lyse the red blood cells. The fixative is present at a concentration that is sufficient to (1) disinfect infectious agents contained in the sample; and (2) fix the leukocytes. As discussed in the detailed description of the invention, the concentration of fixative necessary for simultaneously disinfecting the sample and fixing the leukocytes is, in part, a function of the sample matrix.

Preferably, the biological fluid sample is blood or semen which is fixed prior to determining the presence of an analyte such as a leukocyte component or other non-cellular component (e.g., virus) contained therein. Surprisingly, the instant invention permits amplification of the analyte, e.g., by polymerase chain reaction (PCR) amplification of a known DNA or RNA sequence, following fixation of the biological fluid sample. A thorough discussion of the polymerase chain reaction is disclosed in U.S. Pat. Nos. 4,683,195 and 4,683,202, issued to Mullis, K. B., et al., the entire contents of which are incorporated herein by reference. Modifications of the polymerase chain reaction procedure (e.g., to enhance the sensitivity of antigen detection by attaching an antibody to an oligonucleotide which is subsequently amplified using the polymerase chain reaction; reverse transcriptase PCR ("RT-PCR") to amplify viral RNA), as well as other types of amplification procedures are well known to those of ordinary skill in the art. (See e.g., Science 260:976–979 (1993) for an exemplary protocol for RT-PCR. The entire contents of which are incorporated herein by reference.).

According to yet another aspect of the invention, a method for disinfecting a biological fluid sample and determining the presence of an analyte contained therein is disclosed. Exemplary fixatives, as well as their disinfecting concentrations, are described below. The method involves (a) contacting the sample with a fixative solution containing a fixative present at a disinfecting concentration to form a fixed specimen; (b) allowing the fixed specimen to react with a cognate of the analyte to form an analyte-cognate complex; and (c) detecting the presence of the analyte-cognate complex.

As used herein, "cognate" refers to a molecule that is capable of specifically recognizing and associating with the analyte. Thus, for example, for an analyte that is a DNA or RNA sequence, the cognate is an oligonucleotide that hybridizes to the nucleic acid sequence. Alternatively, the analyte can be an antigen and the cognate is an antibody that specifically recognizes and associates with the antigen. Exemplary analytes include antibodies, antigens (e.g., prostate specific antigen, pathogens such as chlamydia, cytomegalovirus), hormones, oligonucleotides and nucleic acids. The meaning of each of these terms will be immediately apparent to one of ordinary skill in the art. Additional examples of analytes are provided in the Examples.

According to still another aspect of the invention, a kit for disinfecting a biological fluid sample is provided. The kit includes a receptacle for receiving the biological fluid sample and instructions for collecting and disinfecting the sample. The receptacle contains a volume of fixation solution containing a fixative present at a disinfecting concentration for disinfecting a preselected volume of biological fluid sample. Accordingly, the instructions include directions for contacting a specified volume of the sample with the fixation solution contained in the receptacle. In a preferred embodiment, the kit further includes a collection vessel for collecting the biological fluid sample and instructions for transferring the sample (e.g., instructions for transferring a specified volume of sample) to the receptacle. In a most preferred embodiment, the kit further includes a package for transporting the receptacle containing the disinfected sample to a testing facility for analysis.

These and other aspects of the invention, as well as various advantages and utilities will be more apparent with reference to the detailed description of the preferred embodiments and in the accompanying drawings.

DETAILED DESCRIPTION OF THE INVENTION

Figure 1:
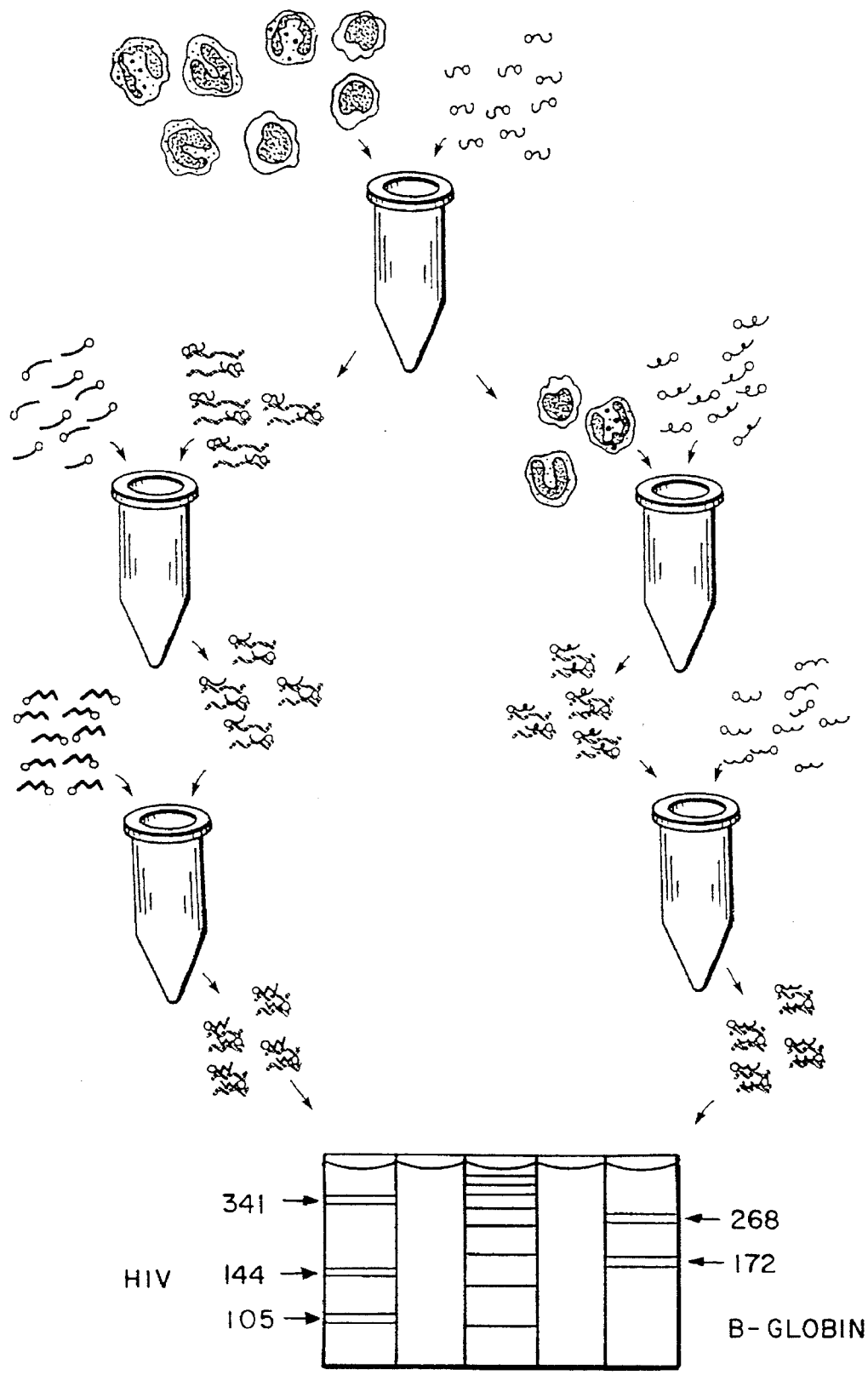
FIG. 1 illustrates a paradigm of a PCR protocol showing the steps involved in amplifying HIV and cell (beta-globin gene) DNAs.

One method for handling a biological fluid sample to reduce the transmission of infectious agents contained therein includes: (a) collecting the biological fluid sample from a donor at a first location; (b) contacting the sample at the first location with a fixation solution containing a fixative to form a fixed specimen; and (c) packaging the fixed specimen for transport to a second location for analysis.

As used herein, the phrase biological fluid sample includes blood and semen. Most preferably, the sample is blood or semen that has been collected (i.e., withdrawn or otherwise obtained) from a human donor. The method of collecting the biological fluid sample is dictated by the nature of the biological fluid. Typically, blood is collected in EDTA-containing vacuum blood tubes or syringes according to standard methods, while semen is collected by ejaculation into condoms or into sterile laboratory containers. (See, e.g., the EXAMPLES). It is believed that the methods of the instant invention also are applicable to other types of clinically-relevant fluids (e.g., sputum, urine).

The first location can include a non-medical setting (e.g., the home of the donor) or a medical setting such as a clinic or field site where samples are collected but not analyzed. Once collected, the sample is simultaneously fixed and disinfected and the fixed specimen is packaged for transport to a second location for analysis. (See, e.g., the EXAMPLES). The second location is a laboratory or other comparable facility which is capable of testing the fixed specimen for the presence of an analyte (i.e., analysis). Thus, disinfection of the biological fluid sample at the first location minimizes the transmission of infectious agents to laboratory personnel responsible for analyzing the sample, as well as to couriers responsible for transport of the packaged specimen from the first to the second location.

Infectious agents (e.g., pathogens and parasites) contained in the above-identified fluid samples include, for example, Human immunodeficiency Virus (HIV), Human T Cell Leukemia Viruses (HTLVs), hepatitis B, hepatitis C, herpes viruses, as well as infectious agents responsible for more widely recognized sexually transmitted diseases such as gonorrhea, syphilis and chlamydiasis. infectious agents present in the biological fluid are inactivated (i.e., disinfected) by contacting the sample with a disinfecting concentration of a fixative.

As used herein, the term "fixative" refers to an agent that is capable of preserving the structure of a biological molecule. Fixatives that are useful for the purposes of the instant invention include the well-known fixatives that are commonly used for flow cytometry and tissue fixation applications. (See, e.g., Lifson, J., et al., *J. Immunol., Methods* 86:143–149 (1986), the entire contents of which are incorporated by reference). These include, for example, paraformaldehyde, formaldehyde and glutaraldehyde. It is believed that fixatives, such as paraformaldehyde, act by crosslinking proteins, with the resulting crosslinked products stabilizing the cellular ultrastructure. (see, e.g., Aloisio, C., and Nicholson, J., *J. Immunol. Methods.* 128:281–285 (1990), the entire contents of which are incorporated by reference, and references cited therein). Also provided herein is a method for evaluating (screening) aldehyde and non-aldehyde (e.g., Streck's Tissue Fixative ("STF")) fixatives for use in accordance with the methods of the invention. (See e.g., *Science* 260:976–979 (1993), the entire contents of which are incorporated herein by reference).

In the preferred embodiments, the fixative solution contains between about 2% and about 10% paraformaldehyde. However, the preferred "disinfecting concentration" for a particular fixative is prescribed, at least in part, by the nature of the biological fluid. Thus, for blood samples in which it is desirable to simultaneously disinfect the sample, lyse the red blood cells and preserve the leukocytes for analysis, the preferred fixative is paraformaldehyde having a disinfecting concentration of between about 2% and about 4%. This is because it is generally believed that paraformaldehyde concentrations less than 2% are not immediately (i.e., within 5–10 minutes) disinfecting, while concentrations greater than 4% fix (not lyse) the red blood cells.

In addition, red blood cell lysis also requires a hypoosmolar medium. Accordingly, in a preferred embodiment, the blood sample is added to the fixation solution to ensure that an immediate drop in osmotic strength is achieved. Red blood cell lysis is evidenced by clearing of the fixation solution to a dark red brown color. (See the Examples). In the most preferred embodiment for simultaneously disinfecting the sample, lysing the red blood cells and preserving the leukocytes for analysis, the preferred fixation solution is hypoosmolar, has a pH greater than about 9.0 and includes 3.0% paraformaldehyde and 2 mM EDTA.

To be useful for the purposes of the instant invention, the fixative must have the ability to (1) rapidly (i.e., within 5–10 minutes following contact) inactivate infectious agents contained in a biological fluid sample (e.g., determined by treating the fluid with a solution containing the putative fixative and observing whether the treated fluid is substantially free of active virus) and (2) preserve the cellular ultrastructure of the biological fluid for subsequent analysis of an analyte contained therein (e.g., by assaying the pre- and post- treatment sample for the presence of an analyte (described below). Thus, selection of a fixative requires knowledge of the sample matrix (e.g., blood or semen), as well as knowledge of the type of analysis to be performed (e.g., immunoassay, polymerase chain reaction amplification, in situ hybridization). To select a disinfecting concentration of a fixative for a particular matrix, the appropriate controls and standards for a particular matrix and analysis method must be included in the screening assays. Thus, for example, negative controls (i.e., samples, standards and buffers that are not exposed to the putative fixative but receive all other manipulations) must be included in the screening process. Once identified as a fixative suitable for use in the methods of the instant invention, the fixative is tested for interference with the analytical method employed for determining the presence of the analyte.

The biological fluid sample is contacted with a disinfecting concentration of the fixative to form a fixed specimen. As used herein, the phrase "fixed specimen" has its conventional meaning known to one of ordinary skill in the art. More particularly with respect to the instant invention, "fixed specimen" refers to a biological fluid sample that has been treated to preserve the structure of cellular (e.g., leukocyte DNA) and non-cellular components (e.g., viral DNA) for analysis.

As used herein, a disinfecting concentration of fixative is that concentration of fixative which is sufficient to inactivate the pathogens contained in the biological fluid sample. According to the Center for Disease Control (Atlanta, Ga.), exposure to aldehyde fixatives at concentrations greater than about 2% results in the inactivation of most pathogens. However, exposure time, temperature, matrix and the state of the pathogen (e.g., whether a viral pathogen is cell-free or cell-associated) also are determinants of disinfectant inactivation. For example, it is generally believed that cell-free virus is substantially more sensitive to inactivating agents and conditions (e.g., heat) in comparison with cell-associated viruses. Accordingly, each of the above-mentioned parameters (concentration, time, temperature) should be considered when selecting a disinfecting concentration of fixative with respect to a particular matrix and suspected pathogen.

Preferably, tissue culture methods are used to determine whether a sample is substantially free of active virus.

Typically, viral inactivation tissue culture studies are based upon viral plaque forming activity in a variety of tissues and a "reduction factor" ("RF") is determined for each putative fixative over a broad concentration range in order to identify the "disinfecting concentration" for the putative fixative in a particular matrix. The Reduction Factor is determined by comparing the virus titer from pre- and post-inactivation treated samples and standards:

$$RF = \text{Log}_{10} \frac{\text{Pre-treatment Virus Titer/Volume} \times \text{Pre-treatment Volume}}{\text{Post-treatment Virus Titer/Volume} \times \text{Post-treatment Volume}}$$

In general, a positive control comprises a standard biological fluid containing a high virus titer (108). The concentration of fixative resulting in a reduction of between about 5–6 logs is considered the disinfecting concentration for the fixative in the particular matrix used for the tissue culture study. Other methods, such as reverse transcriptase activity, antigen capture immunoassays (e.g., HIV determination by the p24 ELISA) and determination of infectious virus titer (ID 50, i.e., the reciprocal of the dilution at which 50% of the cell cultures are positive) also can be used to evaluate the disinfecting ability of a putative fixative and/or to establish a disinfecting concentration for a selected fixative . (See, e.g., Martin, L., et al., *J. Infectious Diseases* 152(2):400–403 (1985), the entire contents of which are incorporated herein by reference).

The term "analyte" as used herein refers to a clinically-relevant component present in the biological fluid sample. Thus, analytes include cells and cellular components, e.g., oligonucleotides, nucleic acids, peptides, proteins and steroids, the presence, absence or relative amount of which is indicative of a medical condition (e.g., infertility, disease or non-disease state). Analytes are measured according to methods known by one of ordinary skill in the art. Such methods include cytologic staining (using stains such as Wright-Giemsa, pananicolaou, hematoxylin, thiazine), immunochemistry to detect cell-free as well as cell-associated proteins and/or peptides (e.g., ELISA, RIA, fluorescence immunoassay), immunocytochemistry to distinguish cell types and changes in protein expression (e.g., immunoassays for quantitating CD 4 and CD 8 receptor expression), receptor assays (e.g., for steroid hormone detection) and hybridization methods (e.g., DNA and/or RNA analysis by Southern and/or Northern analysis, respectively, with or without prior amplification of an oligonucleotide analyte or a sequence contained in a nucleic acid analyte). Inorganic cellular components (e.g., zinc, magnesium) are determined by standard blood chemistry techniques. Exemplary preferred methods of analysis are illustrated in the Examples.

Exemplary analytes that are cellular components include peptides (e.g., antigens), proteins (e.g., antigens such as prostate specific antigen (diagnostic for prostrate cancer), antibodies, hormones), oligonucleotides, and nucleic acids. The term "analytes" also embraces non-cellular components, such as infectious agents (e.g., viruses and viral components including oligonucleotides and proteins) and parasites, as well as compounds which are diagnostic or indicative of a medical condition. Exemplary non-cellular components include viral analytes such as human immunodeficiency virus, chlamydia, cytomegalovirus; parasitic analytes such as the malaria parasite; and compounds including elicit drugs and prescribed medications, the serum level of which must be monitored.

According to a preferred embodiment, the biological fluid sample is disinfected and fixed as described above and the presence of the analyte in the fixed specimen is determined by allowing the fixed specimen to react with a cognate of the analyte to form an analyte-cognate complex. As used herein, the term "cognate" refers to a molecule which is capable of specifically recognizing and associating with an analyte. Accordingly, a cognate is defined in terms of the specific analyte with which it associates. Thus, for example, the cognate for an antigenic peptide or protein is an antibody which specifically recognizes and associates with the peptide or protein to form an antigen-antibody complex. Similarly, the cognate for an oligonucleotide (referred to herein as a "first" oligonucleotide) is a complementary oligonucleotide (referred to herein as a "second" oligonucleotide) which specifically hybridizes to the first oligonucleotide. Detection of the above-mentioned analyte-cognate complexes is in accordance with methods known to one of ordinary skill in the art. (See, e.g., the Examples).

Also within the scope of the invention are kits for disinfecting a biological fluid sample. The kits include a receptacle for receiving the sample, as well as instructions for collecting and disinfecting the sample. The receptacle includes a fixation solution containing a fixative that is present at a disinfecting concentration. The receptacle is further characterized in having a size and dimension sufficient for containing the combined volume of the fixative solution and the biological fluid, yet small enough to be conveniently packaged for transport to a testing facility. Such receptacles are known to one of ordinary skill in the art.

Preferably, the kit further includes a collection vessel for collecting the biological fluid sample and instructions for transferring the sample to the above-described receptacle. Exemplary collection vessels appropriate for a particular biological fluid include are known to one of ordinary skill in the art (e.g., EDTA-containing vacuum blood tubes for collecting blood samples, condoms or other sterile laboratory containers for collecting semen samples). Several types of blood tubes are standard, including those containing EDTA anticoagulant and those containing a silicone polymer that promotes separation of serum from cells. The tubes have a slight vacuum to promote easy blood collection from the vein. Thus, multiple blood samples can be obtained from one venipuncture by simply introducing and filling different tubes in the holding device while the needle is seated in the vein. The tubes of blood are then transported by courier to the clinical laboratory for evaluation. More preferably, the kit further contains a package for sending the receptacle to a testing facility for analyzing the sample contained therein for the presence of an analyte (described above).

The methods of the instant invention thus provide a new approach for handling biological fluids to reduce the risk of transmission of infectious agents contained therein. Working examples illustrating the utility of the invention are presented below.

EXAMPLES

The Examples provided herein illustrate a new process for safely disinfecting and fixing biological fluid samples (e.g., blood and semen) and are not intended to limit the scope of the invention in any way.

METHODS AND MATERIALS

Blood

We have formulated and tested with blood samples several new aldehyde-based fixation solutions. Two solutions have been found to routinely lead to lysis of red blood cells simultaneously with fixation and preservation of nucleated cells in a state recoverable by routine laboratory centrifugation methods. One solution was a dilute phosphate-buffered saline solution (1% DPBS, SIGMA Chemical Co., St. Louis, Mo.) containing between 2.5 to 3.5 gm of paraformaldehyde dissolved per 100 ml. The other was a solution of 10 mM Tris-HCl (SIGMA Chemical Co., St. Louis, Mo.), (pH=9.0–10.5), 4–5 mM EDTA, plus 2.5–3.5 gm of paraformaldehyde per 100 ml. Other buffers may also be appropriate vehicles. Since completing these experiments, we have further optimized the fixation solution and have determined that for most applications, the fixation solution of choice contains 3.0% (w/v) paraformaldehyde, 10 mM Tris base, 2 mM EDTA, in 1% DPBS adjusted to a pH>9.0.

In a preferred embodiment, a ratio of one part blood is added to a minimum of five parts by volume of buffered fixative (i.e., fixation solution) to lower osmolarity in order to achieve red blood cell lysis. Rigid polypropylene (30 cc, Nalgene with polyethylene screw cap, leak proof, Fisher) plastic bottles were loaded with 25 cc of fixation solution and taken to the site of venipuncture. Five ml of blood collected in either EDTA-containing vacuum blood tubes or syringes was added immediately to the formaldehyde solution. Red blood cell lysis occurred on contact as evidenced by clearing of the solution to a dark red brown color. This treatment is believed to inactivate most known pathogens within minutes, thereby significantly improving the safety of sample transport and analysis.

For samples to be sent to a testing facility (i.e., laboratory) for analysis, the bottle was placed inside a two part mailer (Fisher Scientific) which is described as conforming with Interstate Quarantine Regulations for Etiologic Agents (42 CFR, part 72.25). The mailer is composed of a seamless, autoclavable aluminum screw-top container with absorbent packing placed inside a rigid cardboard container with a metal top. The address was written directly on the cardboard container to which appropriate postage was affixed.

The fixed blood cells were recovered from the formaldehyde-blood solution free of hemoglobin and red blood cell membranes by overnight settling or by repeated routine centrifugation and resuspension in fresh fixative containing reduced formaldehyde concentrations. Further analysis is described below.

Semen

A major obstacle to the routine use of semen in diagnoses is the inconvenience associated with collecting ejaculated samples in a laboratory setting. The use of aldehyde-based fixation allowed samples to be collected at remote sites (such as home) and preserved for analyses. Since the usual volume of an ejaculate was 2 to 5 cc, semen ejaculated into condoms or sterile laboratory containers was added to the above-described polypropylene bottles containing 25 cc of buffered fixative. Accordingly, samples collected and fixed at home reduced the risks of pathogen exposure and transmission during transport and evaluation. Fixed semen samples can be evaluated for cell types, proteins and DNA sequences using many of the same methods currently available for analyzing fixed blood cells.

Fixed semen or blood cells were washed free of background proteins, counted with a hemacytometer or automated counter (e.g. such as Coulter), and aliquoted onto slides for routine cytologic-staining. Papanicolaou, hematoxylin without or with eosin, or thiazine stains all accurately delineated nuclei and cytoplasm.

Immunostain

The following commercially available monoclonal antibodies have been found to give accurate and sensitive immunostaining results with the paraformaldehyde-fixed cells: the leukocyte-specific antibodies, HLe-1 (Becton Dickinson) and LC-CD45 (Dako); and prostate specific antigen (PSA, Dako). HLe-1 immunostained all leukocytes, whereas LC stained lymphocytes/monocytes in both blood and semen. Prostate specific antigen stained some cells and protein-containing vesicles in fixed semen. Other antibodies, which are believed to be useful for detecting antigens contained in a formalin-fixed preparation include, e.g. antibodies specific for CD4 and/or CD8 receptor.

Routine immunostaining procedures with biotinylated second antibody and streptavidin-conjugated horseradish peroxidase were performed according to standard procedures. Briefly, an aliquot of the fixed cell suspension was centrifuged at 500×g for 10 minutes, the supernatant solution was removed, and the cell pellet was resuspended in phosphate buffered saline. Aliquots of approximately $10^6$ cells in 5 ul were placed onto 8-spot slides, dried at 60° C. and immunostained with each antibody according to Zymed kit instructions (Histostain SP-kit, Zymed laboratories, San Francisco, Calif.). Briefly, each spot was treated with 1% $H_2O_2$ for 5 min to block endogenous peroxidase activity, washed twice with PBS, and blocked with 10% non-immune rabbit serum for 10 minutes. Following two additional rinses with PBS (phosphate buffered saline), 50 ul drops of monoclonal antibody (diluted 1:10, HLe or PSA, or 1:25, LC) were applied for 30 minutes at 37° C. After rinsing with PBS, biotinylated rabbit anti-mouse immunoglobulin (diluted 1:200) was added for 10 minutes, followed by PBS rinses and treated with streptavidin conjugated horse radish peroxidase for five-minutes. The substrate-chromogen complex (0.03% peroxide and aminoethylcarbazole, AEC) was added for 5 minutes. Slides were rinsed with distilled water and counter-stained with, for example, hematoxylin to visualize nuclei and non-immunoreactive cells.

Polymerase Chain Reaction

Assay conditions and cycling strategy: Our PCR strategy involves a triple amplification of HIV sequences using bracket/nested oligonucleotide primer pairs and conditions customized to optimize specificity as well as yield at each stage of amplification. The strategy includes amplification of single copy gene sequences (e.g. beta-globin) as controls, as illustrated in FIG. 1.

Protease digested, formalin-fixed cells were initially subjected to PCR amplification of a 341 base pair HIV sequence (FIG. 1, top tube). Cells are shown intact in the figure for illustration only, the protease K digestion step destroyed their morphology. Aliquots of reaction products were re-amplified with primers to an inner, 144 base pair HIV sequence (FIG. 1, left center tube) and beta-globin DNA sequences (FIG. 1, right tube). Aliquots of the second reaction tubes were reamplified with primers to an inner, 105 base pair HIV sequence (FIG. 1, left lower tube) and an inner, 160 base pair beta-globin sequence (FIG. 1, right lower tube). Aliquots (10–20 [µl]) of final PCR products were electrophoresed through 8.5% polyacrylamide.

For each amplification procedure, a batch of PCR reaction mixture was prepared from a 10x stock buffer (stored at −20° C.) to which was added Taq DNA polymerase (Perkin Elmer Cetus Corp.) and primers immediately prior to use, in an isolated, "DNA-free" laminar flow hood. All buffers and solutions were prepared from freshly distilled Type I water. Appropriate volumes of mix were aliquotted to reaction tubes in the same hood. Cell samples, DNA controls, or water blanks in one to 10 μl were added in a separate laboratory on a bench which was exposed to UV lights between experiments. The final concentrations of reaction components were: 20 mM Tris (pH 8.8 at 25° C.), 20 mM KCl, 2.0–2.5 mM MgCl$_2$ 100 ug/ml BSA (bovine serum albumin), 0.05% NP40 (nonidet polymer 40, Sigma Chemical Co., St. Louis, Mo.), 4% ethylene glycol, 200 uM each of dATP, dCTP, dGTP and dTTP, plus 1 or 100 picomole(s) of each primer and 0.5 or 2.5 units of Tag DNA polymerase (Perkin Elmer Cetus Corporation) in a 100 ul reaction volume. The PCR temperature controllers (Perkin Elmer and GTC-2) were located in a third Laboratory.

We have had consistently reproducible results amplifying a conserved gag region of HIV I (Genbank Accession No. K02007). The primers used in each reaction were (5' to 3'): TTATCAGAAGGAGCCACCCC (Sequence ID No. 1) and CCTTGTCTTATGTCCAGAATGC (Sequence ID No. 2) for the initial 341 base pair amplicon; AGTGGGGGGA-CATCAAGCAGCCATGCAAAT (Sequence ID No. 3) and cCTGCTATGTCACTTCCCCT (Sequence ID No. 4) for the intermediate 144 base pair amplicon; and GAGACTAT-CAATGAGGAAGC (Sequence ID No. 5) and TGCTATGT-CAGTTCCCCTTGGTTCTCT (Sequence ID No. 6) for the final 105 base ampiicon. The 341 base pair sequence was amplified from I picomole of each primer and 0.5 units of Tag polymerase (to limit non-specific DNA synthesis) for two cycles of 98° C.×2 min; 55° C.×30 sec; 72° C.×15 sec; 18 cycles of 95° C.×I min; 55° C.×30 sec; 72° C.×15 sec, plus a final 2 minute extension at 72° C. after the 20 cycles. Two to ten microliters of these products were transferred to a second reaction set-up (FIG. 1) containing the same PCR buffer, 100 picomoles of each primer for the 144 base pair product, and 2.5 units of Tag polymerase for two cycles of 98° C.×2 min; 55° C.×30 sec; 72° C.×15 sec; 38 cycles of 95° C.×1 min; 55° C.×30 sec; 72° C.×15 sec, plus a final two minute extension at 72° C. after the 40 cycles. For the final amplification, two microliters of the 144 base pair products were transferred to fresh reaction conditions containing 100 picomoles of the primers for the 105 base pair product plus 2.5 units of enzyme for 40 cycles of the same strategy as the second amplification.

Eliminating cross-over contamination of reaction tubes.

Contamination of reaction tubes occurs principally through carry-over of PCR product from previous experiments when PCR reaction tubes are opened for sampling for the next round of amplification. In our laboratories, the strict assignment of a "DNA-free" laboratory for stock buffers, Tag DNA polymerase, deoxyribo-oligonucleotide primers, and set-up paraphernalia was maintained at all times. In order to verify the integrity of the stock reagents, a new water blank was set up for each round of amplification. A selection of rear-closure, disposable lab gowns with elasticized cuffs was maintained in each separate area for use during PCR set-up.

Sample pipetting was performed in laminar flow hoods equipped with UV lights or on lab benches equipped with a UV light source for irradiating the area after use. Volumes of 1 to 10 ul were measured with disposable positive displacement microcapillary pipets (Drummond); the re-useable plunger handles were decontaminated between uses by soaking in a 10% Clorox bleach solution. Volumes greater than 10 ul were measured using Hamilton syringes or Pipetmen (Rainen) equipped with aerosol-resistant tips.

Microcapillary pipetters to be used in sample handling were loaded with plunger rods in the "DNA-free" room and transported to other areas in a sealed test tube. Single-use sample racks were made from leftover, disposable p1000 pipette tip boxes which had their own lids, and a support surface with holes which accommodated 500 ul PCR tubes (Perkin Elmer). Whatman DEAE paper, dampened with dilute HCl was used as an all-purpose DNA trap of PCR products likely to escape from one tube and contaminate the PCR environment or other sample tubes. A layer of DEAE paper acted as a mat on the pipet tip-box surface through which PCR tubes could be easily pushed into the holes of the box. Another layer was placed over the tubes to protect the lids from aerosolized products during sample pipetting. Small swatches of DEAE paper also were used to bonnet each tube as it was opened. This served to catch any aerosolized product and to keep gloved fingertips from distributing product among the other tubes during handling. A mat of DEAE paper was used on the bench or hood surface to delineate the actual pipetting area.

We have found that the standard mineral oil overlay increases the likelihood of carry-over contamination of amplified DNA products and was not required if the lids of the PCR tubes remained heated throughout the amplification process. A weighted heating mat set to 95° C. covering the tubes in the thermal controller block served to inhibit condensation on the lids and promote condensation in the reaction tubes during the cooling cycle.

An additional safeguard against contamination of the laboratory area at large was the use of a disposable plastic chamber for pipetting final PCR samples for electrophoresis. The chamber is a self-contained, plastic wrapped work space (2 ft×1 ft×1 ft) which has disposable sleeves taped into it through which are passed necessary sample setup apparatus prior to opening tubes. The goal was to provide PCR product containment.

Other Analyses.

Other DNA and RNA analytical procedures, including ligase chain reaction, in situ PCR, in situ hybridization are performed on the fixed specimen using methods known to one of ordinary skill in the art.

RESULTS AND DISCUSSION

Cytologic assessment.

The morphology of fixed blood cells in routine cytology was improved by the fixation process as evidenced by more distinct nuclear and cell membranes. A similar improvement was observed for fixed semen cells.

Immunostaining.

The monoclonal antibody, HLe-1 stained all fixed peripheral blood white cells and all fixed leukocytes in semen as determined by a comparison of results in fresh versus formalin-fixed cells from both body fluids.

Monoclonal antibody, HLe-1, immunostained (see Methods for details) all fixed leukocytes as indicated by the red-brown color of the blood cells and the semen leukocytes in comparison with the blue hematoxylin-stained control blood cells and semen cells.

The lymphocyte specific LC antibody also accurately distinguished lymphocytes and monocytes in fixed cell suspensions from other leukocytes with the same specificity as in fresh cell suspensions. Of equal interest was the discovery that monoclonal antibodies specific for prostate specific antigen (PSA, Dako), currently used as a tumor marker for prostatic carcinoma cells, also reacted with formalin-fixed semen cells and free protein, suggesting a new approach for evaluating normal and abnormal numbers of prostate cells and PSA in semen. Neither HLe-1 nor LC reacted with immature germ cells.

Polymerase Chain Reaction.

To be useful as a method of diagnosis for HIV, the polymerase chain reaction should be able to detect a single provirus in a background of approximately $10^6$–$10^7$ cells. For example, in the paradigm described in FIG. 1, this means specific amplification of a single 105 base pair sequence in the presence of $10^{13\text{-}14}$ similar sized sequences in $10^{6\text{-}7}$ cells. Even under stringent conditions of primer annealing, these extremes of template concentrations generally give rise to nonspecific products capable of competing with target DNA sequences for amplification. To minimize such non-specific synthesis, the initial HIV amplification reaction was designed to generate HIV amplicons in quantities equivalent to the number of cells by limiting the concentration of primers and enzyme. Thus, the second amplification begins with a sample from the first that contains HIV sequences approximately equivalent to single gene copies per cell.

The goal of the second HIV amplification reaction was to take advantage of the specificity conferred by a primer set internal to the first ampiicon, thus selecting against nonspecific DNA products bearing the original primer sequences, and to carry out sufficient replication to yield products approximately equivalent in concentration to cell DNA. The third amplification reaction further restricted the specificity of the reaction to only HIV sequences and generated sufficient copies (approximately $10^{11}$) of the 105 base pair sequence for detection by routine ethidium bromide staining following acrylamide gel electrophoresis. A single copy human gene sequence such as beta-globin or LDL receptor was amplified in parallel assays as a control for the presence of amplifiable DNA.

PCR Amplification of DNA Sequences in Formaldehydr-Fixed White Blood Cells.

Figure 2:
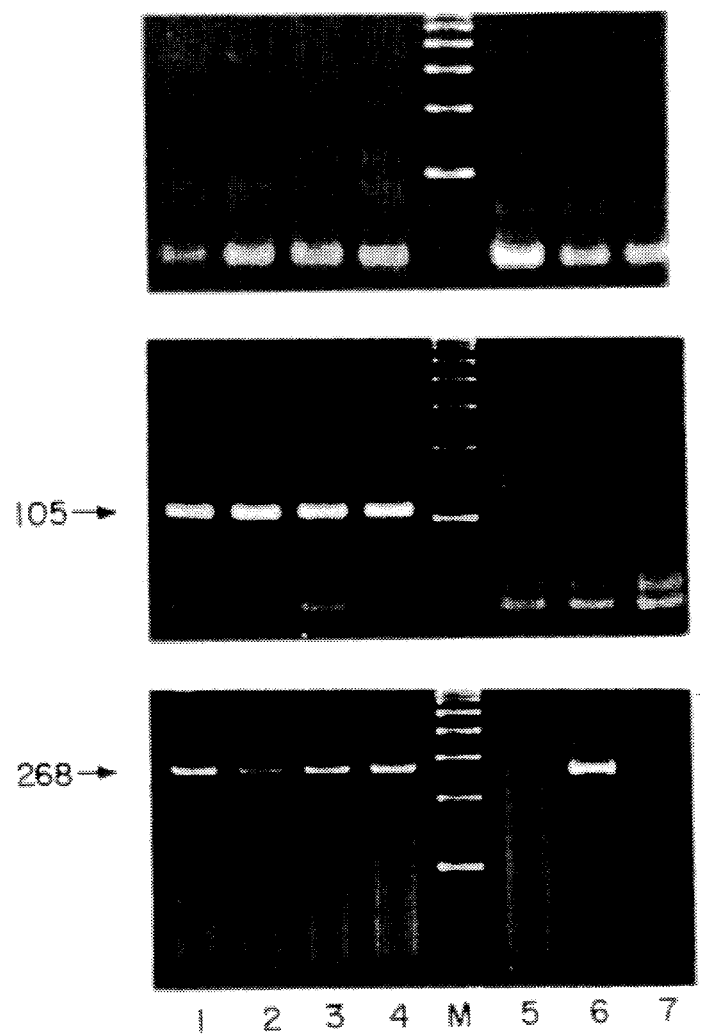
FIG. 2 illustrates PCR amplification of DNA sequences contained in formaldehyde fixed white blood cells (leukocytes)

Reconstruction experiments have determined that 5 copies of HIV control plasmid DNA were readily detectable in a background of 106 formalin-fixed white blood cells (FIG. 2). Formaldehyde-fixed cells from four HIV-negative donors were subjected to PCR analysis as outlined in FIG. 1. 20 µl aliquots of final PCR products were electrophoresed through 8.5% polyacrylamide gels and stained with ethidium bromide. FIG. 2, Top panel: Lanes 1–4, $10^6$ cells from each donor, triple-amplified for HIV gag sequences; lanes 5–7, reagent blanks initiated during each round of amplification, respectively. FIG. 2, Center panel: White Blood cells from two of the normal donors spiked with 5 (lanes 1 and 3) or 50 (lanes 2 and 4) copies of HIV control plasmid syc1857 and amplified as above for HIV-gag sequences. Lanes 1 and 2, $10^6$ cells from donor #1; lanes 3 and 4, $10^6$ cells from donor #2; lanes 5–7, blanks as above. Bottom panel: 2 µl of products from the first round of HIV amplification ($10^4$ cell equivalents of white blood cell genomic DNA) were reamplified with β-globin primers. Lanes 1–5 directly corresponded to samples depicted in lanes 1–5, center panel; lane 6, $10^4$ cell equivalents of placental DNA was run as a positive control for β-globin PCR; lane 7, reagent blank. M, 100 base pair ("bp") ladder control DNA marker.

The detection was specific as no similar bands were observed in HIV-negative blood cells (FIG. 2, upper panel) which contained PCR amplifiable DNA as evidenced by the beta-globin DNA bands (FIG. 2, lower panel).

PCR amplification of HIV DNA sequences in formaldehyde fixed peripheral blood cells from an HIV-infected hemophiliac.

Figure 3:
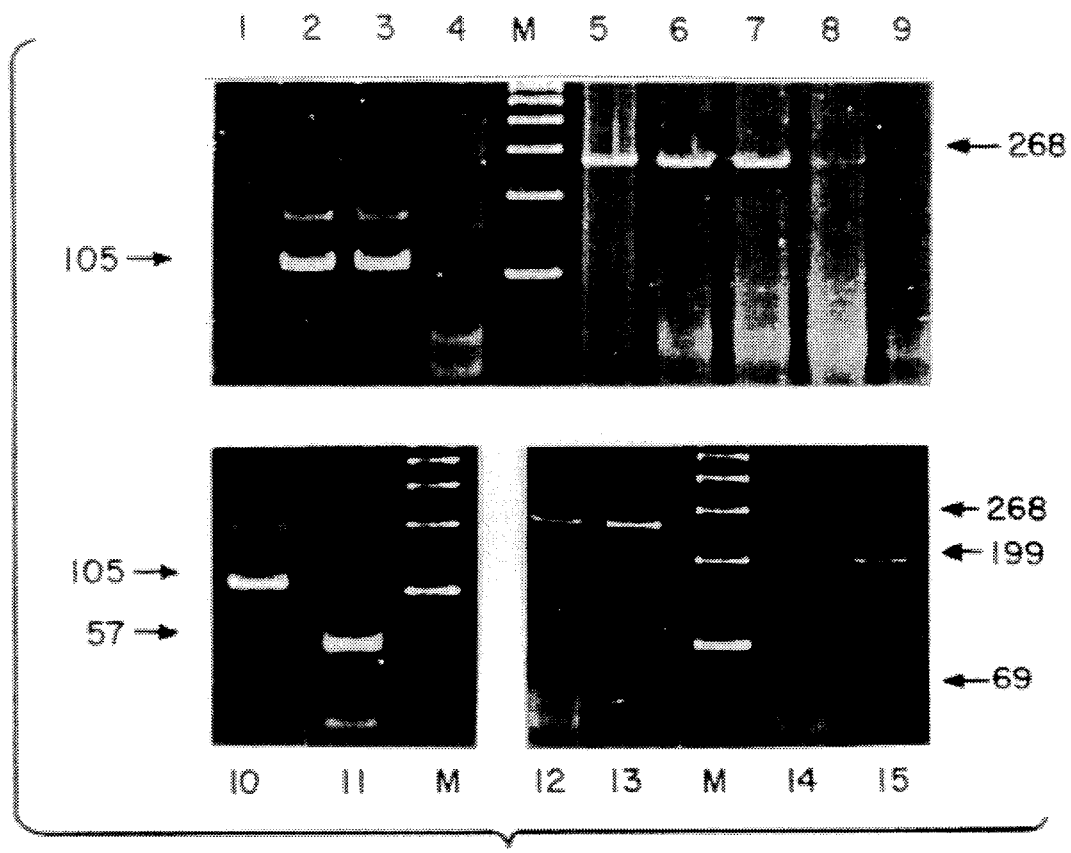
FIG. 3 illustrates PCR amplification of HIV DNA sequences in formaldehyde fixed white blood cells (leukocytes) from an HIV-infected hemophiliac.

FIG. 3, Upper panel: Ethidium bromide stained bands of HIV gag (lanes 1–4) and β-globin (lanes 59) DNA amplified sequences from formaldehyde-fixed white blood cells of an HIV seropositive hemophiliac by the PCR paradigm described in FIG. 1. Lanes 1–4 are final DNA products from 0, $1\times10^5$, $3\times10^4$, and $1\times10^4$ cells in the initial PCR reaction, respectively; lanes 6–8 are β-globin DNA sequences amplified from 1/10 of the initial HIV reaction mixtures of lanes 2–4, respectively; lane 5 contains β-globin DNA products amplified as control from 50 ng ($1\times10^4$ cell equivalents) purified human placenta DNA; lane 9 was an aliquot of a beta-globin PCR reaction containing no DNA. Lower panel: Hae Ill restriction digest analysis of PCR products from the upper panel experiment. HIV gag, white blood cell β-globin and placental (β-globin PCR products are shown in lanes 10, 12 and 13 with their corresponding Hae III digestion fragments run in lanes 11 (57, 34 and 14 bp), 14 and 15 (199 and 69 bp), respectively.

Thus, the method similarly detected HIV sequences in white blood cells from a seropositive patient (FIG. 3, upper panel), clearly delineating that at least one in $3\times10^4$ (but not one in $1\times10^4$) blood cells were HIV-infected. Accordingly, the instant invention provides a powerful approach to quantifying the level of infection of peripheral blood cells. That the DNA sequences amplified were those targeted was verified by digestion with restriction nuclease which yielded fragments of the expected sizes (FIG. 3, lower panel).

Amplification of LDL receptor genomic DNA sequences in fresh and formalin-fixed sperm.

Aliquots of cryopreserved sperm were thawed and divided into two parts: one part was fixed with five volumes of formalin (as described in Methods). Each part was washed, counted, and digested with protease K as described for blood cells. Aliquots were subjected to bracket/nested PCR reactions in the same buffer and cycling conditions as described in Methods with the substitution of LDL receptor specific primers derived from Genbank Accession Nos. L00347K02573 and L00348K02573 (5' to 3'): AGTGC-CAACCGCCTCACAG (Sequence ID No. 7) (LrM1) and CCTCTCACACCAGTTCACTC (Sequence ID No. 8) (LrM4) for the initial amplification (at a final concentration of 100 picomoles each), and substituting TGGCTGGGT-GAGGTTGTGGA (Sequence ID No. 9) (LrM6) for LrM4 in the second round of hemi-nested amplification, each primer at a final concentration of 100 picomoles each. Odd numbered lanes contain samples from fixed semen; even numbered lanes from non-fixed semen; lanes 1 and 2, $10^6$ cells; 3 and 4, $10^7$ Cells; 5 and 6, $10^5$ cells; 7 and 8, $10^4$ cells; P=50 ng ($10^4$ cell equivalents of placenta DNA control; B=no DNA assay blank; M=Hae III digested phiX 174 molecular size marker.

Figure 4:
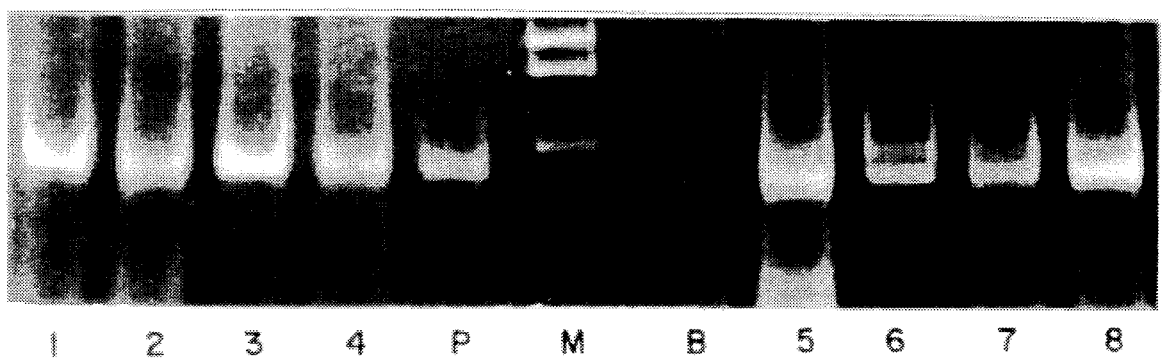
FIG. 4 illustrates amplification of LDL receptor genomic DNA sequences in freshly isolated and formalin-fixed sperm.

Similar results have been obtained with infected semen samples. In addition, specific single copy gene sequences previously amplified from unfixed semen samples for the purpose of genetic haplotyping of single sperm (*Proc. Acad. Sci. USA* 87:4580–4584 (1990), the entire contents of which are incorporated herein by reference) were also amplifiable from formalin-fixed sperm (FIG. 4); a nested amplification detected as few as $10^3$ sperm.

CONCLUSIONS

These Examples illustrate a new approach for markedly improving the sensitivity and safety of evaluating and transporting pathogen-infected cells in both clinical and research settings. The methods described here have wide application for safer evaluation of blood and semen from all sources, thus providing a new, rapid means of evaluating and improving upon therapies for infectious pathogens.

It should be understood that the preceding is merely a detailed description of certain preferred embodiments. It therefore should be apparent to those skilled in the art that various modifications and equivalents can be made without departing from the spirit or scope of the invention.

A Sequence Listing immediately follows. The Sequence Listing is followed by what is claimed.

I claim:

1. A method for processing a biological fluid sample containing red blood cells and leukocytes, the method comprising:
   (a) contacting the biological fluid sample with an amount of a hypoosmolar fixative solution that is sufficient to simultaneously
      (I) disinfect the biological fluid sample,
      (ii) fix the biological fluid sample to form a fixed specimen comprising a suspension of fixed leukocytes and fixed non-cellular components, and
      (iii) lyse the red blood cells,
   wherein the fixative solution contains between about 2% and about 10% of a fixative selected from the group consisting of glutaraldehyde, paraformaldehyde and formaldehyde.

2. The method of claim 1, wherein the biological fluid sample comprises blood.

3. The method of claim 1, wherein the fixative comprises paraformaldehyde.

4. The method of claim 1, wherein the fixative solution contains between about 2% and about 4% of the fixative.

5. The method of claim 1, further comprising the step of (b) detecting the presence of an analyte in the fixed specimen.

6. The method of claim 5, wherein detecting the presence of he analyte comprises allowing the fixed specimen to react with a cognate of the analyte to form an analyte-cognate complex and detecting the analyte-cognate complex.

7. The method of claim 5, wherein the analyte is a leukocyte component.

8. The method of claim 5, wherein the analyte is a non-cellular component.

9. The method of claim 5, further comprising the step of amplifying the concentration of the analyte prior to detecting the analyte.

10. The method of claim 5, wherein the analyte is selected from the group consisting of a peptide, a protein, an oligonucleotide and a nucleic acid.

11. The method of claim 10, wherein the analyte comprises a nucleic acid and the cognate comprises an oligonucleotide that hybridizes to a sequence contained in the nucleic acid.

12. The method of claim 10, wherein the analyte comprises an antigen and the cognate comprises an antibody that specifically recognizes and associates with the antigen.

13. The method of claim 10, wherein the analyte comprises an antibody and the cognate comprises an antigen that is specifically recognized by and associates with the antibody.

14. A method for processing a biological fluid sample comprising:
   (a) contacting the biological fluid sample with an amount of a fixative solution that is sufficient to simultaneously
      (I) disinfect the biological fluid sample, and
      (ii) fix the biological fluid sample to form a fixed specimen comprising a suspension of fixed cellular and fixed non-cellular components,
   wherein the fixative solution contains between about 2% and about 10% of a fixative selected from the group consisting of paraformaldehyde, formaldehyde and glutaraldehyde and wherein the biological fluid sample comprises semen.

15. The method of claim 14, wherein the fixative comprises paraformaldehyde.

16. The method of claim 14, wherein the fixative solution contains between about 2% and about 4% paraformaldehyde.

17. The method of claim 14, further comprising the step of (b) detecting the presence of an analyte in the fixed specimen.

18. The method of claim 17, wherein detecting the presence of the analyte comprises allowing the fixed specimen to react with a cognate of the analyte to form an analyte-cognate complex and detecting the analyte-cognate complex.

19. The method of claim 17, wherein the analyte is a leukocyte component.

20. The method of claim 17, wherein the analyte is a non-cellular component.

21. The method of claim 17, further comprising the step of amplifying the concentration of the analyte prior to detecting the analyte.

22. The method of claim 17, wherein the analyte is selected from the group consisting of a peptide, a protein, an oligonucleotide and a nucleic acid.

23. The method of claim 22, wherein the analyte comprises a nucleic acid and the cognate comprises an oligonucleotide that hybridizes to a sequence contained in the nucleic acid.

24. The method of claim 22, wherein the analyte comprises an antigen and the cognate comprises an antibody that specifically recognizes and associates with the antigen.

25. The method of claim 22, wherein the analyte comprises an antibody and the cognate comprises an antigen that is specifically recognized by and associates with the antibody.

26. A kit for processing a biological fluid sample, the kit comprising:

a receptacle for receiving the biological fluid sample, the receptacle including an amount of a fixative solution that is sufficient to simultaneously (I) disinfect the biological fluid sample, and (ii) fix the biological fluid sample to form a fixed specimen comprising a suspension of fixed cellular and fixed non-cellular components, wherein the fixative solution contains between about 2% and about 10% of a fixative selected from the group consisting of paraformaldehyde, formaldehyde and glutaraldehyde and wherein the biological fluid sample comprises a semen sample or a red blood cell containing sample, provided that if the sample comprises a red blood cell containing sample, the fixative solution further is sufficient to simultaneously lyse the red blood cells contained therein; and instructions for collecting and disinfecting the biological fluid sample.

* * * * *